(12) United States Patent
Kamegawa (10) Patent No.: US 7,792,242 B2  
(45) Date of Patent: *Sep. 7, 2010

(54) X-RAY CT SYSTEM AND X-RAY CT METHOD

(75) Inventor: Masayuki Kamegawa, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 445 days.

This patent is subject to a terminal disclaimer.

(21) Appl. No.: 11/719,274

(22) PCT Filed: Oct. 26, 2005

(86) PCT No.: PCT/JP2005/019691

§ 371 (c)(1),  
(2), (4) Date: May 14, 2007

(87) PCT Pub. No.: WO2006/051690

PCT Pub. Date: May 18, 2006

(65) Prior Publication Data

US 2009/0074136 A1    Mar. 19, 2009

(30) Foreign Application Priority Data

Nov. 12, 2004 (JP) .............................. 2004-328401  
Jan. 6, 2005 (JP) ........................... P2005-001826

(51) Int. Cl.  
G01N 23/00 (2006.01)

(52) U.S. Cl. ............................. 378/20; 378/63; 378/98; 378/207

(58) Field of Classification Search ............... 378/4, 378/20, 63, 91, 98, 114–117, 204–210  
See application file for complete search history.

(56) References Cited

U.S. PATENT DOCUMENTS 4,894,855 A * 1/1990 Kresse ........................ 378/196  
5,917,876 A * 6/1999 Fujii et al. ..................... 378/4  
7,016,465 B2 * 3/2006 Kamegawa ................... 378/63  
7,258,485 B2 * 8/2007 Nakano et al. ............... 378/205

FOREIGN PATENT DOCUMENTS

| JP | 61-013941 A | 1/1986 |
| JP | 01-131645 A | 5/1989 |
| JP | 4-158208 A | 6/1992 |
| JP | 6-49284 Y2 | 12/1994 |

(Continued)

OTHER PUBLICATIONS

Japanese Office Action dated Nov. 4, 2009 in Application No. 2005-001826.  
Japanese Office Action dated Mar. 3, 2010 in corresponding Japanese application No. 2005-001826.

Primary Examiner—Jurie Yun  
(74) Attorney, Agent, or Firm—Sughrue Mion, PLLC (57) ABSTRACT

There are provided an X-ray CT system and an X-ray CT method in which a subject can be brought as close as possible to an X-ray source at all times while preventing interference of the subject with the X-ray source at the time of rotation, without confirmation by an operator by rotating a rotary stage before CT projection.

A subject W placed on a rotary stage 3 is captured by an optical camera 6, and information about a shape, a size and a position relative to a rotational axis R, of the subject W, are acquired by image processing using captured data. Then, interference between the subject W and an X-ray source 1 is monitored on the basis of the information, or the rotary stage 3 is automatically positioned at a location where the subject approaches most closely to the X-ray source 1 without interference.

13 Claims, 8 Drawing Sheets

FOREIGN PATENT DOCUMENTS

| | | |
|---|---|---|
| JP | 7-128258 A | 5/1995 |
| JP | 2002-62268 A | 2/2002 |
| JP | 2002-310943 A | 10/2002 |
| JP | 2002-357567 A | 12/2002 |
| JP | 2004-45212 A | 2/2004 |
| JP | 2004-117024 A | 4/2004 |
| JP | 2004-301861 A | 10/2004 |
| JP | 2004-317226 A | 11/2004 |

\* cited by examiner

X-RAY CT SYSTEM AND X-RAY CT METHOD

TECHNICAL FIELD

The present invention relates to an industrial X-ray CT system and an industrial X-ray CT method for acquiring a tomogram in order to nondestructively inspect internal defects, an internal structure and the like, of an industrial product such as an electronic component.

BACKGROUND ART

In an industrial X-ray CT system, generally, a rotary stage which rotates around an axis orthogonal to an X-ray optical axis is arranged between an X-ray source and an X-ray detector, which are disposed opposite each other. X-rays are irradiated onto a subject in a state the subject is held on the rotary stage. X-ray transmission data are obtained from the X-ray detector every time the rotary stage is rotated by a predetermined minute angle. A tomogram of the subject taken along a plane orthogonal to a rotational axis of the rotary stage is reconstructed by using the obtained X-ray transmission data (see, e.g., Patent Document 1). The rotary stage is usually movable in a direction of the X-ray optical axis (direction of the x-axis) and in directions orthogonal thereto (directions of the y-axis and the z-axis) by a moving mechanism. There is known an X-ray CT system provided with an xy table on the rotary stage, for moving the subject in two directions (directions of the x-axis and the y-axis) orthogonal to the rotational axis.

Patent Document 1: Japanese Patent Laid-Open Publication No. 2004-117024

DISCLOSURE OF THE INVENTION

Problem to be Solved by the Invention

Incidentally, in the field of the industrial X-ray CT system as mentioned above, for instance, when a tomogram about a neighborhood of a semiconductor chip mounted on a circuit board is to be acquired, a subject must be brought as closely as possible to the X-ray source for reasons such as a desire to increase scaling factor as high as possible and a desire to acquire the tomogram as bright as possible. Since the subject must be rotated while being placed on the rotary stage during CT projection, an operator adjusts the position of the rotary stage prior to actual CT projection by rotating the rotary stage with the subject being placed on the rotary stage and checking a distance to the X-ray source through an observation window. The rotary stage is set so as to get closer to a degree immediately before the position where the subject interferes with the X-ray light source. However, there is a problem that the operation is laborious.

Moreover, in an apparatus in which the xy table is provided on the rotary stage and a desired position on the subject can be moved to a neighborhood of the rotation center, the above adjusting operation must be again performed after the xy table has been moved, to thus determine whether the X-ray source is not subjected to interference. This operation is a cause of a drop in working efficiency.

Moreover, in a case of a so-called half-scan photography in which the subject is rotated for about a little more than a half-turn (corresponding, in reality, to the sum of 180° and a spread angle of X-rays) for performing CT projection, and the reconstruction is performed, the subject can be made get closer to the X-ray source to a much greater extent. Particularly, this is effective for a case where areas to be observed are shifted from the center of the subject during observation of soldered sections of an IC package or the like on a printed wiring board. In this case, attention must be paid to the direction of rotation of the subject and the setting of a distance between the subject and the X-ray source.

In order to obtain a desired tomogram, it goes without saying that X-ray transmission data for all points on the tomogram are required. However, depending on scaling factor or the like based on positions of the rotary stage and the X-ray detector with respect to the X-ray source in the X-ray optical axis direction, there may arise a case where the requirement is not fulfilled. In the X-ray CT system, prior to acquiring the X-ray transmission image data of the subject, the subject is rotated for one turn while being placed on the rotary stage and being exposed to X-ray radiation, and whether or not the subject is placed at a position where the desired tomogram can be acquired from the X-ray fluoroscopic image acquired from moment to moment is checked. Depending on the checking result, the position must be changed, which in turn poses a problem that the operation is laborious.

The present invention has been made to solve the drawbacks in the related-art industrial X-ray CT system. The principal object of the present invention is to provide an X-ray CT system and an X-ray CT method, which prevent occurrence of an interference with an X-ray source during rotation of a subject, and do not require a checking operation performed by an operator by rotating a rotary stage before CT projection.

Another object of the present invention is to provide an X-ray CT system which do not require an operator to pay special consideration to a distance between a subject and an X-ray source and the rotating direction of a rotary stage even at the time of selecting half-scan operation.

Still another object of the present invention is to provide an X-ray CT system so that whether or not a desired tomogram can be acquired can be intuitively understood.

Means for Solving the Problems

In order to solve the above-described principal problems, an X-ray CT system of the present invention including: a rotary stage which is arranged between an X-ray source and an X-ray detector which are arranged opposite to each other and rotates around a rotational axis orthogonal to an X-ray optical axis while holding a subject; and a reconstruction computing section for reconstructing a tomogram of the subject along a plane orthogonal to the rotational axis, by using X-ray transmission data of the subject that is obtained for every predetermined angle while the rotary stage is being rotated, the X-ray CT system comprising:

an optical camera which captures the subject on the rotary stage from a position along the rotational axis of the rotary stage or a position close to the rotational axis;

an image processing section which acquires information related to shape, size and a position relative to the rotational axis, of the subject, from an external image of the subject captured by the optical camera; and an interference monitoring section which monitors an interference between the subject and the X-ray source during rotation of the rotary stage by using the information acquired by the image processing section.

As a specific configuration of the interference monitoring section of the present invention, there can be adopted a configuration for determining whether the subject interferes with the X-ray source during the rotation of the rotary stage based on positions of the X-ray source and the rotary stage and the information acquired by the image processing section, and when the subject interferes with the X-ray source, issuing an alarm indicating as such, or similarly, a configuration for determining whether the subject interferes with the X-ray source during the rotation of the rotary stage based on positions of the X-ray source and the rotary stage and the information acquired by the image processing section, and when the subject interferes with the X-ray source, prohibiting the rotation of the rotary stage.

In the X-ray CT system, there can also be adopted a configuration in which when half-scan is selected, the interference monitoring section monitors the interference by limiting a rotating direction of the rotary stage to a direction in which the rotary stage can approach more closely to the X-ray source in a way that the subject does not interfere with the X-ray source.

In the present invention, there can also be adopted a configuration further comprising a rotary stage position setting section, in place of the interference monitoring section as claimed in claim 1, which sets a position of the rotary stage in which the rotational axis of the rotary stage approaches most closely to the X-ray source and the subject does not interfere with the X-ray source during the rotation of the rotary stage, by using the information acquired by the information processing section.

Even in the X-ray CT system having the rotary stage position setting section, there can also be adopted a configuration in which when half-scan is selected, the rotary stage position setting section sets the position of the rotary stage by limiting a rotating direction of the rotary stage to a direction in which the rotary stage can approach more closely to the X-ray source in a way that the subject does not interfere with the X-ray source. As in the case of the previously-described X-ray CT apparatus, the operator is not required to pay consideration to the rotating direction or the like of the subject when the half-scan is selected, and the other problem of the present invention can be solved.

The above-described X-ray CT system preferably adopts a configuration comprising: a CT projection area computing section for calculating an area where CT projection is available around the rotational axis as a center, by using information about a positional relationship among the X-ray source, the X-ray detector and the rotary stage in a direction of the X-ray optical axis, and a size of a light-receiving surface of the X-ray detector; and a display section which superimposes the area calculated by the CT projection area computing section on an image of the subject captured by the optical camera so as to display the image on an display.

Further, the X-ray CT system preferably adopts a configuration comprising: a CT projection area computing section for calculating an area where CT projection is available around the rotational axis as a center, by using information about a positional relationship among the X-ray source, the X-ray detector and the rotary stage in a direction of the X-ray optical axis, and a size of a light-receiving surface of the X-ray detector;

a display section which superimposes the area calculated by the CT projection area computing section on an image of the subject captured by the optical camera so as to display the image on an display; and a control section which moves the X-ray detector or the subject in the direction of the X-ray optical axis in conjunction with a change of a size of the area displayed on the display section.

An X-ray CT system of the present invention is an invention whose principal constituent elements are identical with those of the previously-described X-ray CT system; and includes: a rotary stage which is arranged between an X-ray source and an X-ray detector which are arranged opposite to each other and rotates around a rotational axis orthogonal to an X-ray optical axis while holding a subject; and a reconstruction computing section for reconstructing a tomogram of the subject along a plane orthogonal to the rotational axis, by using X-ray transmission data of the subject that is obtained for every predetermined angle while the rotary stage is being rotated, the X-ray CT system comprising:

an optical camera which captures the subject on the rotary stage from a position along the rotational axis of the rotary stage or a position close to the rotational axis;

an image processing section which acquires information related to shape, size and a position relative to the rotational axis, of the subject, from an external image of the subject captured by the optical camera; and a subject evacuating section which moves the subject to the outside of a field of view of the X-ray detector upon performing air calibration of an X-ray, by using the information acquired by the image processing section.

The present invention is intended to solve the principal problems by:

acquiring information about a shape, a size and a position relative to the rotational axis, of the subject, from an external image of the subject being captured by an optical camera from a position along the rotational axis of the rotary stage or a position close to the rotational axis; and monitoring an interference between the subject and the X-ray source during rotation of the rotary stage in the X-ray CT system, or positioning the rotary stage at a position where the subject approaches most closely to the subject without the interference.

Specifically, the subject held on the rotary stage is captured by the optical camera from a position on the rotational axis of the rotary stage or a neighborhood thereof, whereby the information about the shape, the size and the position relative to the rotational axis of the rotary stage, of the subject, can be acquired. When the subject is rotated at the position of the rotary stage (i.e., the position of the rotational axis) acquired at the present time, a determination can be made as to whether or not the X-ray source is subjected to interference, from the information. When it is determined that the interference occurs, the X-ray CT system performs monitoring, such as issuance of an alarm, and prohibition of rotation of the rotary stage.

Moreover, the X-ray CT system automatically performs the positioning, on the basis of the information, to a position where the rotational axis of the rotary stage approaches most closely to the X-ray source and where the subject does not interfere with the X-ray source; namely, a position where scaling factor and brightness become maximum.

By such monitoring or positioning operation, operations for checking occurrence/nonoccurrence of interference and re-positioning operation prior to CT projection are obviated.

The above X-ray CT system determines, when the half-scan is selected, a direction in which the subject can approach more closely to the X-ray source in a way that the subject does not interfere with the X-ray source, from an external image of the subject on the rotary stage; limits the rotating direction of the rotary stage to that direction; and performs monitoring operation or positioning of the rotary stage.

In addition to the function of monitoring the interference or setting the position of the rotary stage to an optimal position, the X-ray CT system can calculate an area where the CT projection is possible by geometrical calculation by using a positional relationship among the X-ray source, the X-ray detector and the rotational axis of the rotary stage. By superimposing the calculated area on the external image of the subject captured by the optical camera and displaying the thus-superimposed area, whether or not the desired tomogram can be acquired can be intuitively understood without checking the fluoroscopic images captured from moment to moment by rotating the rotary stage while irradiating the X-rays, prior to CT projection. As a result of combination of this function with a function for monitoring the interference of the subject with the X-ray source or a function for automatically positioning the rotary stage, the operator's operation to be performed prior to CT projection can be significantly reduced. By the function of the interference monitoring section or the function of the setting section, a determination can be promptly made as to whether or not a tomogram covering the intended area can be acquired in the state where the rotary stage is brought closer to the X-ray source as much as possible. Hence, when the area is not covered, a usage is available such as to move the rotary stage away from the X-ray source while the closest position is taken as a starting point.

As mentioned above, the X-ray CT system can calculate an area where the CT projection is possible by geometrical calculation by using a positional relationship among the X-ray source, the X-ray detector and the rotational axis of the rotary stage. The X-ray CT system superimposes the calculated area on the external image of the subject captured by the optical camera and displays the thus-superimposed area, and further moves the X-ray detector or the subject in the direction of the X-ray optical axis in conjunction with the time when the size of the displayed area has been changed, namely, controls the X-ray detector or the subject such that the area intended for projection falls within an actual area where the CT projection is possible. As a result, the operator can intuitively make a desired change of the projection area such that the subject does not interfere with the X-ray source during projection. Accordingly, operator's operation to be performed prior to the CT projection can be significantly reduced.

The X-ray CT system uses the information about the shape, the size and the position relative to the rotational axis of the rotary stage, of the subject, obtained by an optical camera and the image processing section equivalent to those employed in the above-described respective inventions, for air calibration of the X-rays. Air calibration is a procedure indispensable for accurately obtaining radiation distribution of brightness of X-rays before performing CT projection. In reality, after determination of a tube voltage and a tube current of the X-ray source and a distance between the X-ray source and the X-ray detector, X-rays are irradiated to the X-ray detector in a state that the subject is placed outside the field of view of the X-ray detector after having been removed from the rotary stage. Outputs from the X-ray detector are summated, to thus acquire a reference image for determining a 100% level of each pixel. When the distance between the X-ray source and the X-ray detector is changed or when the size of the area of the X-ray detector is changed (i.e., when a multi-image tube is used), air calibration must be performed again. By using the information about the shape, the size and the position relative to the rotational axis, of the subject, acquired by the image processing employing the external image of the subject, the rotary stage is moved and/or when an xy table is placed on the rotary stage, the xy table is moved, thereby automatically causing the subject to evacuate from the view field of the X-ray detector.

ADVANTAGES OF THE INVENTION

According to the present invention, the interference (collision) between the X-ray source and the subject can be prevented although the operator does not pay special attention, and the subject can be caused to get closer to the X-ray source as immediately as possible, to thus readily acquire a bright fluoroscopic image and high scaling factor.

According to the X-ray CT system, when the half-scan is selected, a rotating direction, in which the subject can be caused to get closer to the X-ray source in a way that the interference with the X-ray source does not occur during rotation of the subject, is determined. Especially, in a case where a partial tomogram of a plate-like subject such as a printed-wiring board is acquired at a scaling factor as high as possible, a tomogram at high magnification power is readily acquired without the operator paying attention to the rotating direction of the rotary stage or a distance to the X-ray source.

According to the X-ray CT system, the area where the CT projection is possible that is determined by the position of the X-ray source, the position of the X-ray detector, and the position of the rotary stage is displayed while being superimposed on the external image of the subject. Hence, in combination with the function for causing the subject to get closer to the X-ray source as closely as possible without occurrence of the interference, operations to be performed prior to the CT projection can be significantly reduced. Further, a tomogram of the intended area can be readily acquired at the maximum magnification power.

Further, in the X-ray CT system, by using the information of the shape, the size and the position relative to the rotational axis, of the subject, which are obtained through image processing using the external image of the subject, the subject is automatically moved to the outside of the field of view of the X-ray detector during air calibration. Therefore, even in a case where the distance between the X-ray source and the X-ray detector has been changed or the like, the calibration operation can be facilitated.

BRIEF DESCRIPTION OF THE DRAWINGS

[FIG. 4] (A) A plan view showing an example state where a rotary stage 3 is positioned by a stage position setting section 16d of the embodiment of the present invention, and (B) a side view showing an example state where the rotary stage 3 is positioned by the stage position setting section 16d of the embodiment of the present invention.

[FIG. 6] (A) An operation descriptive view when an xy table 5 is moved according to the embodiment of the present invention, and a plan view of the state before the xy table 5 moves, and (B) an operation descriptive view when the xy table 5 is moved according to the embodiment of the present invention, and a front view of the state before the xy table 5 moves.

[FIG. 7] (A) An operation descriptive view when the xy table 5 is moved according to the embodiment of the present invention, and a plan view of the state after the xy table 5 moved, and (B) an operation descriptive view when the xy table 5 is moved according to the embodiment of the present invention, and a front view of the state after the xy table 5 moved.

[FIG. 8] (A) A descriptive view of the way to limit the rotating direction of a subject W when half-scan is selected in the embodiment of the present invention, and (B) a descriptive view of the way to limit the rotating direction of the subject W when the half-scan is selected in the embodiment of the present invention.

DESCRIPTION OF THE REFERENCE NUMERALS

1 X-ray source
2 X-ray detector
3 Rotary stage
4 Stage moving mechanism
5 xy table
6 Optical Camera
13 CT image reconstruction computing device
14 Display
15 Image data capturing circuit
16 Computation controller
16a Image processing section
16b Image synthesis section
16c CT projection area computing section
16d Stage position setting section
16e Drive control section
L X-ray optical axis
R Rotational axis
W Subject

BEST MODE FOR IMPLEMENTING THE INVENTION

An embodiment of the present invention will be described hereunder by reference to the drawings.

Figure 1:
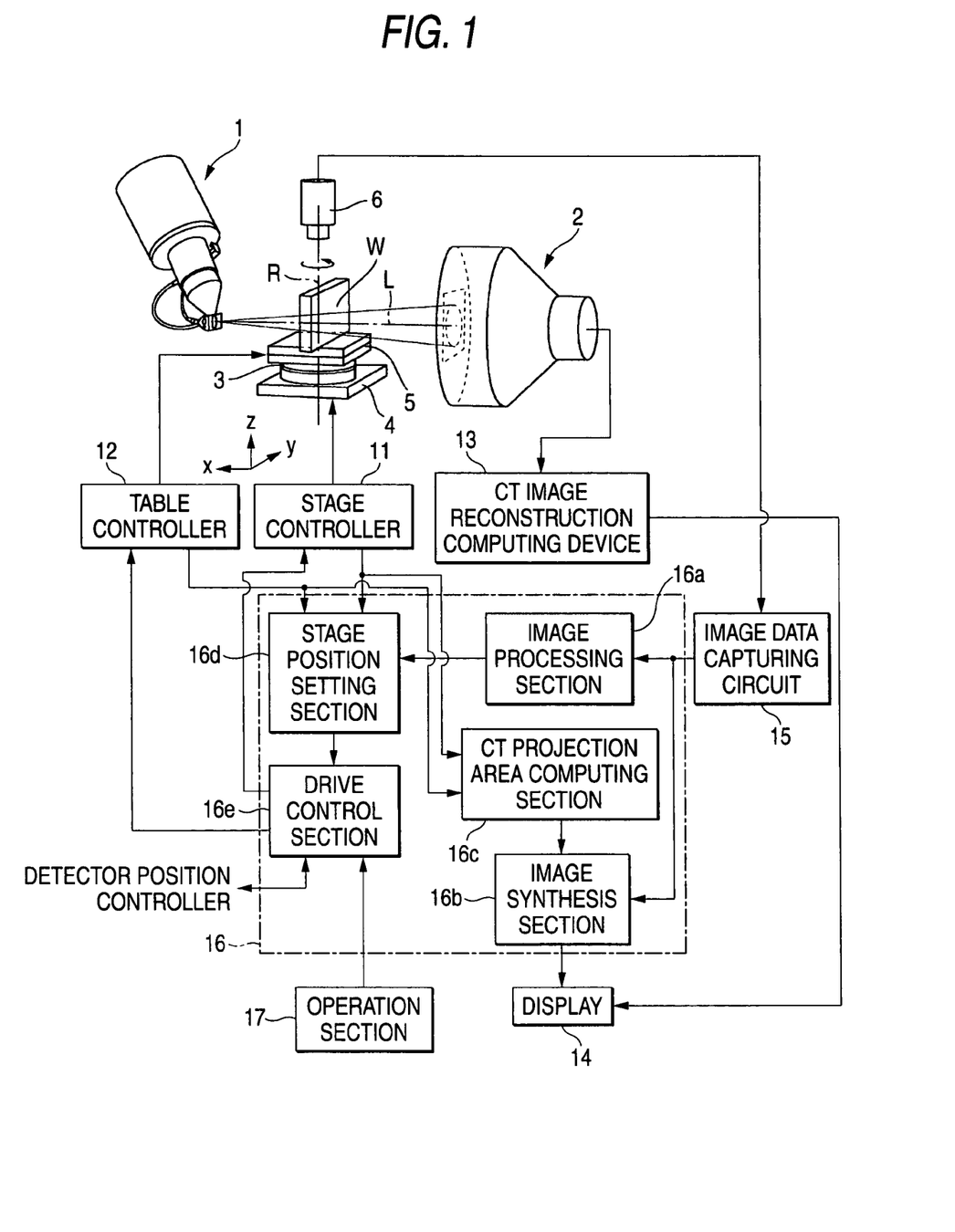
[FIG. 1] A block diagram of an embodiment of the present invention, and a diagram representing both a schematic diagram showing a mechanical configuration and a block diagram showing a system configuration.

FIG. 1 is a block diagram of an embodiment of the present invention, and a diagram representing both a schematic diagram showing a mechanical configuration and a block diagram showing a system configuration.

An X-ray detector 2 is disposed opposite to an X-ray source 1, and a rotary stage 3 for giving a rotation to a subject W is arranged therebetween. The rotary stage 3 is rotated around a rotational axis R in the direction of a z-axis which is orthogonal to the direction of an x-axis aligned along an X-ray optical axis L from the X-ray source 1, and can be moved in any of the directions of x-axis, y-axis, and z-axis, which are orthogonal to each other, by a stage moving mechanism 4. The rotary stage 3 and the stage moving mechanism 4 are driven and controlled by a drive signal supplied from a stage controller 11. Moreover, an xy table 5 to be moved in the directions of the x-axis and the y-axis while mounting the subject W is provided on the rotary stage 3, and this xy table 5 is driven and controlled by the drive signal supplied from the table controller 12. The X-ray detector 2 can move in the direction of the x-axis, and the position of the X-ray detector can be changed in the direction of the x-axis by a drive signal supplied from an unillustrated detector position controller.

For CT projection, the subject W is placed on the xy table 5 and rotated around the rotational axis R while X-rays are irradiated, and a CT image reconstruction computing device 13 acquires X-ray transmission data from the X-ray detector 2 for every minute rotational angle. By using the thus-acquired X-ray transmission data pertaining to 360° of the subject W (180°+θ for the case of half-scan to be described later), the CT image reconstruction computing device 13 constructs a tomogram of the subject W that is sliced by a plane along an x-y plane orthogonal to the rotational axis R, and displays the thus-constructed image on an display 14.

Above the rotary stage 3 and the xy table 5, an optical camera 6 including a CCD, a lens and the like, is disposed along the rotational axis R at a position while being oriented in a vertically-downward direction. The optical camera 6 is coupled to the stage moving mechanism 4 by a column (not shown) or the like, moved in association with movement of the rotary stage 3 in the directions of the x-axis, the y-axis and the z-axis, and positions on the rotational axis R of the rotary stage 3.

A video signal from the optical camera 6, i.e., a video signal pertaining to the rotary stage 3, the xy table 5, and the subject W positioned thereon, is captured by an image processing section 16a and an image synthesis section 16b of a computation controller 16 via an image data capturing circuit 15.

The image processing section 16a obtains a shape, a size and a positional relationship in relation to the rotational axis R, of the subject W, by using the video signal from the optical camera 6. The image synthesis section 16b synthesizes an external image of the subject W captured by the optical camera 6 with an area where CT projection is possible obtained by a CT projection area computing section 16c to be described later, and displays the thus-synthesized image on the display 14. In reality, the computation controller 16 is formed by a computer and peripheral devices thereof, and operates so as to realize the functions of installed programs. However, for the sake of convenience, FIG. 1 shows the computation controller 16 in the form of a block diagram made up of respective functional blocks of the installed program. In addition to the display 14 and the image data capturing circuit 15, an operation section 17 for issuing a command for moving the rotary stage 3, the xy table 5 and the X-ray detector 2 through manual operation or other various commands is connected to the computation controller 16.

Figure 2:
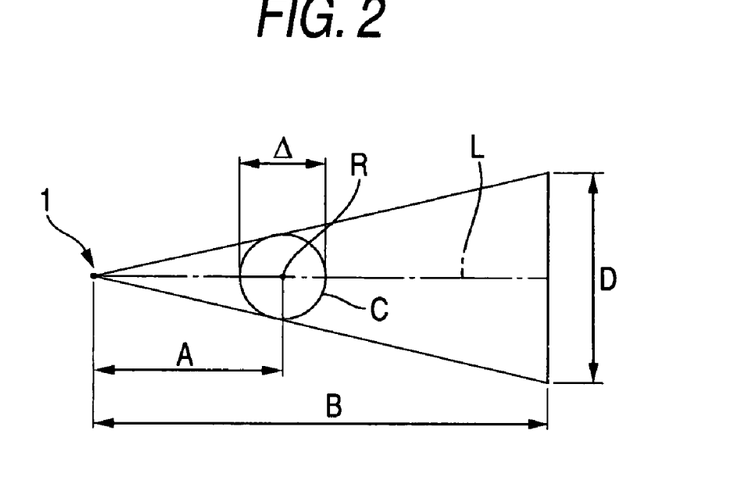
[FIG. 2] A descriptive view of a calculation method of a diameter of a circle C in an area where CT projection is possible in a CT projection area computing section 16c of the embodiment of the present invention.
Figure 3:
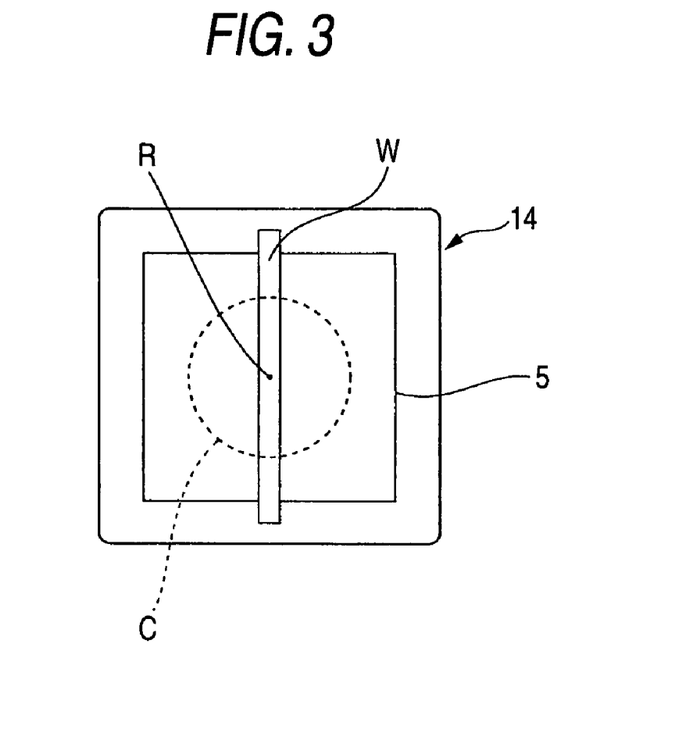
[FIG. 3] A descriptive view of an example display on a display 14 of the embodiment of the present invention.

The CT projection area computing section 16c calculates a circle representing the area where the CT projection is possible which is centered on the rotational axis R, by geometrical calculation using positional information about the rotary stage 3 and the X-ray detector 2 from the stage controller 11 and the detector position controller, and using an effective width of a light-receiving surface of the X-ray detector 2. Specifically, as indicated in FIG. 2 in the form of a plan view, a diameter Δ of the circle C representing the area where CT projection is possible can be calculated as $$\Delta = D \times A/B \quad (1),$$

provided that a distance between the X-ray source 1 (hereinafter, a focal point) and the rotational axis R in the direction of the x-axis is taken as A; a distance between the X-ray source 1 and the light-receiving surface of the X-ray detector 2 in the direction of the x-axis is taken as B; and the effective width of the light-receiving surface of the X-ray detector 2 in the direction of the y-axis is taken as D. As in the case of an example display on the display 14 in FIG. 3, the circle C whose diameter Δ has been calculated as mentioned above is synthesized with the external image of the subject W by the image synthesis section 16b, and the thus-synthesized image is displayed on the display 14.

By using information about the shape and the size of the subject W and the position of the subject W relative to the rotational axis R supplied from the image processing section 16a, the stage position setting section 16d obtains the position of the rotary stage 3 where the X-ray source 1 is spaced apart by a preset minute clearance, from a circle plotted by a point on the subject W which is most distant from the rotational axis R when the subject W is rotated around the rotational axis R for 360°. The stage position setting section 16*d* supplies a drive control signal to the stage controller 11 via a drive control section 16*e* in order to automatically move the rotary stage 3 to that position.

Operation of the embodiment of the present invention will now be described along with the using method.

First, the subject W is placed on the xy table 5 while the rotary stage 3 and the xy table 5 are set at specified positions, e.g., starting point, and an output from the optical camera 6 is captured. The image processing section 16*a* extracts the contour of the subject W, and acquires the shape, the size and the positional relationship to the rotational axis R, of the subject W.

Figure 4:
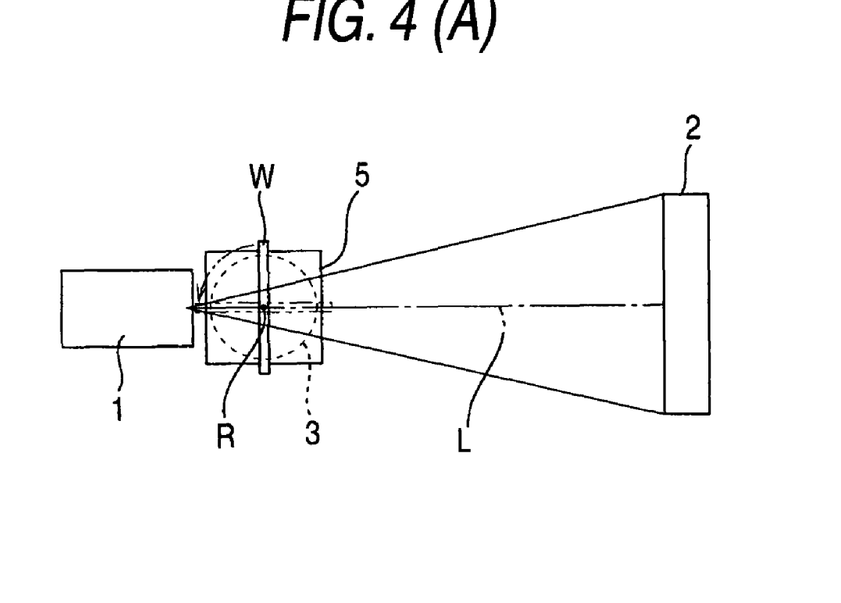

When CT projection is instructed, the stage position setting section 16*d* supplies the drive signal to the rotary stage 3 via the drive control section 16*e* and the stage controller 11, in order to move the rotary stage 3 to a position where the stage is brought closest to the X-ray source 1 and the subject W does not interfere with the X-ray source 1 when the subject W is rotated around the rotational axis R. The state after the movement is shown in the form of a plan view in FIG. 4(A) and in the form of a side view in FIG. 4(B). Thus, minimum SOD is set by which X-ray fluoroscopic data of the brightest subject W having the highest magnifying power can be acquired.

In this state, a determination is made, from a display of the display 14, as to whether or not a intended area falls exactly within the circle C representing the area where CT projection is possible. When a negative determination has been made, the X-ray detector 2 is moved in the direction of the x-axis, thereby determining an SID. In relation to determination of this SID, there can also be adopted a configuration where after the operator changes the size of the circle C displayed on the display 14 to a circle C' through operation of the operation section 17, the X-ray detector 2 is automatically moved in such a way that the circle C as the actual area where CT projection is possible matches with the circle C' specified by the operator.

In the above descriptions, the X-ray detector 2 is moved in the direction of the x-axis in connection with the adjustment for matching the area intended for projection with the circle C. However, the subject W may also be moved in the direction of the x-axis for the purpose of this adjustment. To this end, the position of the subject may be adjusted by manually or automatically actuating the stage moving mechanism 4.

Specifically, the following is also possible. A determination is made, from the display of the display 14, as to whether or not the intended area falls exactly within the circle C representing the area where CT projection is possible. When a negative determination has been made, the stage moving mechanism 4 is driven to thus move the subject W in the direction of the x-axis and determine the SOD. At the time of determination of the SOD, after the operator has changed the size of the circle C displayed on the display 14 to the circle C' through operation of the operation section 17, the subject W is automatically moved in the direction of the x-axis by actuation of the stage moving mechanism 4 in such a way that the circle C corresponding to an actual area where CT projection is possible matches with the circle C' specified by the operator.

Figure 5:
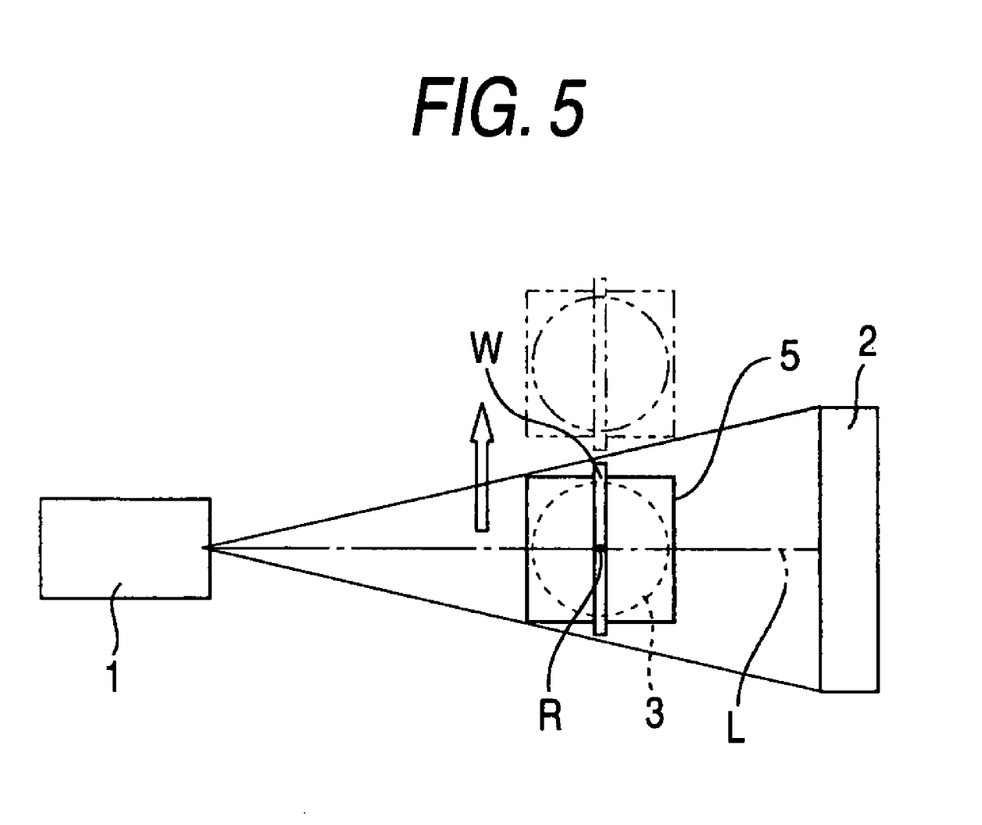
[FIG. 5] A descriptive view of an example of movement of the rotary stage 3 during an air calibration in the embodiment of the present invention.

When air calibration is instructed, the stage position setting section 16*d* supplies the rotary stage 3 and/or the xy table 5 with a drive signal via the drive control section 16*e*, the stage controller 11 and/or the table controller 12, in order to automatically move the rotary stage 3 and/or the xy stage 5 in the direction of the y-axis or in the direction of the x-axis in addition such that the subject W positions outside the field of view of the X-ray detector 2 as shown in FIG. 5, based on the information about the shape, the size and the position relative to the rotational axis R, of the subject, that are supplied from the image processing section 16*a*. Then, the air calibration is performed in this state. After performance of air calibration, the rotary stage 3 and/or the xy table 5 are returned to their positions before the air calibration is performed.

Subsequently, after the operator has moved the rotary stage 3 in the direction of the z-axis so as to acquire a desired sliced plane, CT projection is performed.

Figure 6:
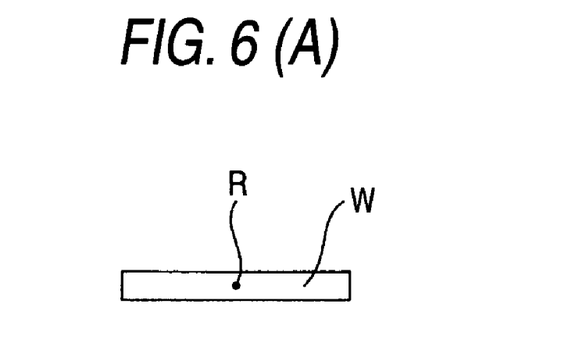
Figure 7:
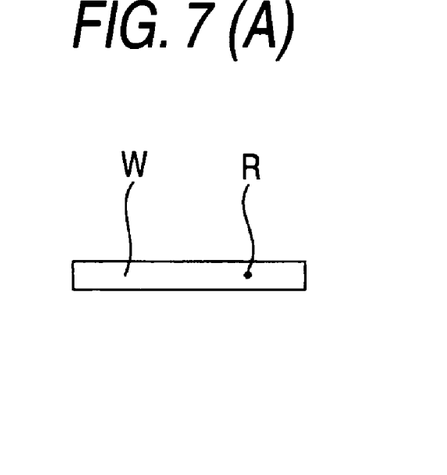

In the above descriptions, a case where the xy table 5 is not moved (except for air calibration) is described. However, when the xy table 5 has been moved, the rotary stage 3 is changed as follows in accordance with the amount of movement. Specifically, for example, as a plan view shown in FIG. 6(A) and a front view shown in FIG. 6(B), when a printed wiring board is taken as the subject W and an IC chip Wa in the center part of the board in the direction of the y-axis thereof is being observed, in relation to the distance between the X-ray source 1 and the rotational axis R, the stage position setting section 16*d* positions the rotary stage 3 such that a distance between the rotational axis R and the X-ray source 1 in the direction of the x-axis becomes (B/2)+δ, provided that the width of the subject W is taken as B and the preset minute clearance is taken as δ. As a plan view is shown in FIG. 7(A) and a front view is shown in FIG. 7(B), when the xy table 5 has been moved for a distance "y" in the direction of the y-axis, a distance from the rotational axis R to the most distant point on the subject W becomes (B/2)+y. Hence, the distance between the rotational axis R and the X-ray source 1 in the direction of the x-axis is automatically changed to (B/2)+y+δ in association with movement of the xy table 4.

According to the above-described embodiment of the invention, the subject W can be brought as closely as possible to the X-ray source 1 in a way that the operator is not required to perform the checking prior to CT projection and the subject W does not interfere with the X-ray source 1. Further, CT projection can be performed at high magnifying power. Further, even when projection is performed at the same magnifying power, X-ray fluoroscopic data as bright as possible are obtained, and an image with a good SN ratio is obtained. Even when the xy table 5 has been moved, operation for checking interference of the X-ray source 1 with the subject W is not required.

Figure 8:
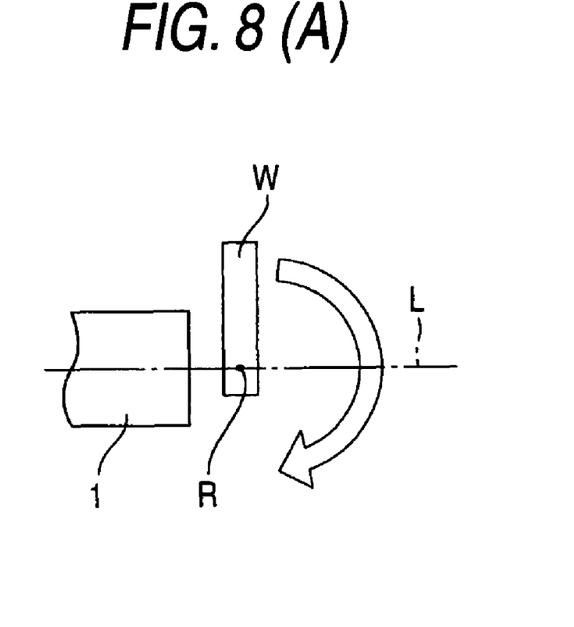
Figure 9:
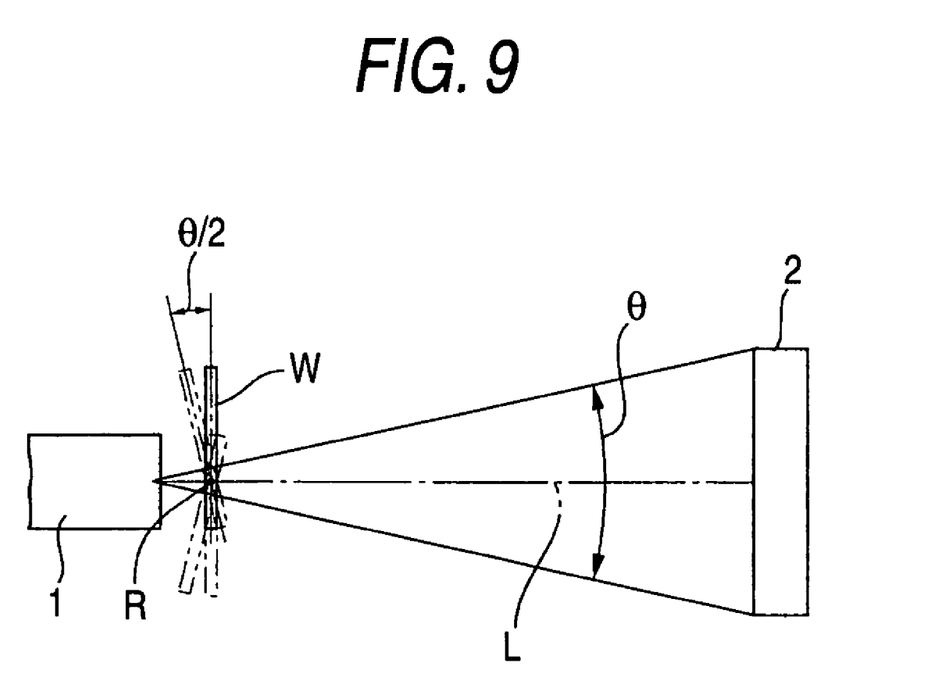
[FIG. 9] A plan view of a principal section showing an example of a state in which the subject W is positioned when the half-scan is selected in the embodiment of the present invention.

Operation performed when half-scan has been selected will now be described. Half-scan enables further shortening of SOD when a position that is shifted from the center of the subject is photographed in an enlarged manner, especially as for the plate-like subject W. However, attention must be paid to the rotating direction of the subject W as mentioned previously. In the embodiment of the present invention, when half-scan has been selected, the rotating direction of the rotary stage 3 is limited, based on the information about the shape, the size and a position relative to the rotational axis R, of the subject W, supplied from the image processing section 16*a*, to a direction in which the position on the subject W most distant from the rotational axis R moves away from the X-ray source 1, as the plan views shown in FIGS. 8(A) and 8(B). In addition, as a plan view is shown in FIG. 9, the rotary stage 3 is positioned at a position where the subject W can maintain the minute clearance θ with respect to the X-ray source 1 when the subject W is rotated for 180°+θ (θ denotes a spread angle of X-rays).

By operation performed during half-scan in the embodiment of the present invention, an optimal SOD is set by just selecting the half-scan, without the operator paying attention to the rotating direction of the subject W and checking the position of the rotary stage 3 by trial and error. In a case where CT projection is performed with large magnifying power on neighborhoods of a plurality of IC chips mounted on such a printed wiring board as mentioned previously, or the like, a burden on the operator can be eased significantly.

As for the optical camera 6, the camera is positioned immediately above the rotational axis R or neighborhood thereof at all times in order to perform projection on the subject W as described in the above embodiment. In addition to that, the optical camera 6 may also be configured so as to be fixed to a system frame or the like, and such that the rotational axis R positions immediately below the optical camera 6 by, e.g., positioning the rotary stage 3 at the origin position and such that the external image of the subject W is photographed in that state and stored. In this case, the external image of the subject W to be displayed on the display 14 by being synthesized with the circle C representing the area where CT projection obtained by the CT projection area computing section 16c, may be the image photographed and stored in advance.

The above-described embodiment has provided the example where the rotary stage 3 is positioned at the position where the subject W is brought as closely as possible to the X-ray source 1 in a way that the subject W does not interfere with the X-ray source 1, based on the information about the shape, the size and the position relative to the rotational axis R, of the subject W, obtained by the image processing section 16a. However, there may also be adopted a configuration where, when the rotary stage 3 is moved by manual operation, a determination is automatically performed, in accordance with the position of the rotary stage 3 acquired from moment to moment, as to whether or not the subject W interferes with the X-ray source 1 when the rotary stage 3 is rotated at that position, and where an interference of the subject W with the X-ray source 1 is monitored by issuing an alarm, prohibiting rotation or the like, in accordance with the result of determination.

The present patent application is based on Japanese Application No. 2004-328401 filed on Nov. 12, 2004 in Japan, the contents of which are hereby incorporated by reference.

The invention claimed is:

1. An X-ray CT system, comprising:
a rotary stage which is arranged between an X-ray source and an X-ray detector which are arranged opposite to each other and rotates around a rotational axis orthogonal to an X-ray optical axis while holding a subject;
a reconstruction computing section for reconstructing a tomogram of the subject along a plane orthogonal to the rotational axis, by using X-ray transmission data of the subject that is obtained for every predetermined angle while the rotary stage is being rotated;
an optical camera which captures the subject on the rotary stage from a position along the rotational axis of the rotary stage or a position close to the rotational axis;
an image processing section which acquires information related to shape, size and a position relative to the rotational axis, of the subject, from an external image of the subject captured by the optical camera;
an interference monitoring section which monitors an interference between the subject and the X-ray source during rotation of the rotary stage by using the information acquired by the image processing section;
a CT projection area computing section for calculating an area where CT projection is available around the rotational axis as a center, by using information about a positional relationship among the X-ray source, the X-ray detector and the rotary stage in a direction of the X-ray optical axis, and a size of a light-receiving surface of the X-ray detector; and
a display section which superimposes the area calculated by the CT projection area computing section on an image of the subject captured by the optical camera so as to display the image on a display.

2. The X-ray CT system according to claim 1, wherein the interference monitoring section determines whether the subject interferes with the X-ray source during the rotation of the rotary stage based on positions of the X-ray source and the rotary stage and the information acquired by the image processing section, and when the subject interferes with the X-ray source, issues an alarm indicating as such.

3. The X-ray CT system according to claim 1, wherein the interference monitoring section determines whether the subject interferes with the X-ray source during the rotation of the rotary stage based on positions of the X-ray source and the rotary stage and the information acquired by the image processing section, and when the subject interferes with the X-ray source, prohibits the rotation of the rotary stage.

4. The X-ray CT system according to claim 1, wherein when half-scan is selected, the interference monitoring section monitors the interference by limiting a rotating direction of the rotary stage to a direction in which the rotary stage can approach more closely to the X-ray source in a way that the subject does not interfere with the X-ray source.

5. The X-ray CT system according to claim 1, further comprising:
a control section which moves the X-ray detector or the subject in the direction of the X-ray optical axis in conjunction with a change of a size of the area displayed on the display.

6. An X-ray CT system, comprising:
a rotary stage which is arranged between an X-ray source and an X-ray detector which are arranged opposite to each other and rotates around a rotational axis orthogonal to an X-ray optical axis while holding a subject;
a reconstruction computing section for reconstructing a tomogram of the subject along a plane orthogonal to the rotational axis, by using X-ray transmission data of the subject that is obtained for every predetermined angle while the rotary stage is being rotated;
an optical camera which captures the subject on the rotary stage from a position along the rotational axis of the rotary stage or a position close to the rotational axis;
an image processing section which acquires information related to shape, size and a position relative to the rotational axis, of the subject, from an external image of the subject captured by the optical camera;
a rotary stage position setting section which sets a position of the rotary stage in which the rotational axis of the rotary stage approaches most closely to the X-ray source and the subject does not interfere with the X-ray source during the rotation of the rotary stage, by using the information acquired by the information processing section;
a CT projection area computing section for calculating an area where CT projection is available around the rotational axis as a center, by using information about a positional relationship among the X-ray source, the X-ray detector and the rotary stage in a direction of the X-ray optical axis, and a size of a light-receiving surface of the X-ray detector; and
a display section which superimposes the area calculated by the CT projection area computing section on an image of the subject captured by the optical camera so as to display the image on a display.

7. The X-ray CT system according to claim 6, wherein when half-scan is selected, the rotary stage position setting section sets the position of the rotary stage by limiting a rotating direction of the rotary stage to a direction in which the rotary stage can approach more closely to the X-ray source in a way that the subject does not interfere with the X-ray source.

8. The X-ray CT system according to claim 6, further comprising:
a control section which moves the X-ray detector or the subject in the direction of the X-ray optical axis in conjunction with a change of a size of the area displayed on the display.

9. An X-ray CT system, comprising:
a rotary stage which is arranged between an X-ray source and an X-ray detector which are arranged opposite to each other and rotates around a rotational axis orthogonal to an X-ray optical axis while holding a subject;
a reconstruction computing section for reconstructing a tomogram of the subject along a plane orthogonal to the rotational axis, by using X-ray transmission data of the subject that is obtained for every predetermined angle while the rotary stage is being rotated;
an optical camera which captures the subject on the rotary stage from a position along the rotational axis of the rotary stage or a position close to the rotational axis;
an image processing section which acquires information related to shape, size and a position relative to the rotational axis, of the subject, from an external image of the subject captured by the optical camera;
a subject evacuating section which moves the subject to the outside of a field of view of the X-ray detector upon performing air calibration of an X-ray, by using the information acquired by the image processing section;
a CT projection area computing section for calculating an area where CT projection is available around the rotational axis as a center, by using information about a positional relationship among the X-ray source, the X-ray detector and the rotary stage in a direction of the X-ray optical axis, and a size of a light-receiving surface of the X-ray detector; and
a display section which superimposes the area calculated by the CT projection area computing section on an image of the subject captured by the optical camera so as to display the image on a display.

10. The X-ray CT system according to claim 9, further comprising:
a control section which moves the X-ray detector or the subject in the direction of the X-ray optical axis in conjunction with a change of a size of the area displayed on the display.

11. An X-ray CT method in an X-ray CT system including an X-ray source and an X-ray detector which are arranged opposite to each other, and a rotary stage which is arranged between the X-ray source and the X-ray detector and rotates around a rotational axis orthogonal to an X-ray optical axis while holding a subject, X-ray CT method comprising:
acquiring first information about a shape, a size and a position relative to the rotational axis, of the subject, from an external image of the subject being captured by an optical camera arranged at a position along the rotational axis of the rotary stage or a position close to the rotational axis;
calculating an area where CT projection is available around the rotational axis as a center, by using second information about a positional relationship among the X-ray source, the X-ray detector and the rotary stage in a direction of the X-ray optical axis, and a size of a light-receiving surface of the X-ray detector;
displaying an image in which the calculated area and the external image are superimposed;
monitoring an interference between the subject and the X-ray source during rotation of the rotary stage by using the first information; and
reconstructing a tomogram of the subject along a plane orthogonal to the rotational axis by using X-ray transmission data of the subject that is obtained for every predetermined angle while the rotary stage is being rotated.

12. The X-ray CT method according to claim 11, further comprising:
moving the subject to the outside of a field of view of the X-ray detector upon performing air calibration of an X-ray, by using the first information.

13. The X-ray CT method according to claim 11, further comprising:
moving the X-ray detector or the subject in the direction of the X-ray optical axis in conjunction with a change of a size of the area displayed on the display.

* * * * *